United States Patent [19]

Kiss

[11] 4,169,201

[45] Sep. 25, 1979

[54] NOVEL ESTER PRECURSOR INTERMEDIATES AND ANTIPODES FOR THE PREPARATION OF 1-(2-TETRAHYDROFURYL)-5-FLUOROURACIL

[75] Inventor: Joseph Kiss, Arlesheim, Switzerland

[73] Assignee: Hoffmann-La Roche Inc., Nutley, N.J.

[21] Appl. No.: 797,898

[22] Filed: May 17, 1977

[30] Foreign Application Priority Data

May 28, 1976 [AT] Austria .................................. 3939/76

[51] Int. Cl.$^2$ ............................................ C07D 405/04
[52] U.S. Cl. ..................... 544/313; 544/243; 544/310
[58] Field of Search ................ 260/260; 544/310, 313, 544/243

[56] References Cited

U.S. PATENT DOCUMENTS

| | | | |
|---|---|---|---|
| 2,949,451 | 8/1960 | Hoffer | 260/260 |
| 3,635,946 | 1/1972 | Giller et al. | 536/23 |
| 4,039,546 | 8/1977 | Giller et al. | 260/260 |

OTHER PUBLICATIONS

Horwitz et al., Cancer Research 35, 1301-1304 (May 1975).

*Primary Examiner*—Paul M. Coughlan, Jr.
*Attorney, Agent, or Firm*—Jon S. Saxe; George M. Gould; James H. Callwood

[57] ABSTRACT

The present disclosure relates to a compound of the general formula:

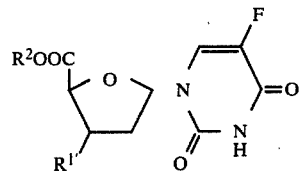

and the novel antipodes of that compound.

3 Claims, No Drawings

NOVEL ESTER PRECURSOR INTERMEDIATES AND ANTIPODES FOR THE PREPARATION OF 1-(2-TETRAHYDROFURYL)-5-FLUOROURACIL

BACKGROUND OF THE INVENTION 1-(2-Tetrahydrofuryl)-5-fluorouracil is a known compound having cytostatic activity and slight toxicity [see Doklady Akademii Nauk SSSR, 176, 332–335 (1967)]. The compound has, however, hitherto been known only as the racemate since the previous processes for its manufacture are not stereospecific (see, for example, United States Patent No. 3,635,946, Belgian Pat. No. 807,556 and Japanese Patent Application No. 116079/1973) and the racemate cannot readily be split into the optical antipodes because of the absence of suitable acidic or basic substituents in the molecule. Also, the enzymatic cleavage of the racemate with glycosidases has been found, because of slight specificity, to be unsuitable for the manufacture of the antipodes in pure form, irrespective of the fact that thereby one of the two anomers disappears.

DESCRIPTION OF THE INVENTION

The present invention is concerned in one aspect with the two optically active antipodes of the aforementioned compound, namely with (2′R)- and (2′S)-1-(2-tetrahydrofuryl)-5-fluorouracil. The (2′S)-antipode is preferred.

In another aspect, the present invention is concerned with a process for the manufacture of the aforementioned antipodes and of racemic 1-(2-tetrahydrofuryl)-5-fluorouracil. This process is advantageous since the starting materials are accessible from an otherwise worthless by-product, namely the α-anomers which are obtained in the manufacture of fluorouracildesoxyuridine.

The process provided by the present invention for the manufacture of 1-(2-tetrahydrofuryl)-5-fluorouracil as the racemate or in the form of an optical antipode comprises hydrogenating racemic or optically active 1-(2,3-dihydro-2-furyl)-5-fluorouracil.

In a preferred embodiment of the foregoing process, optically active 1-(2,3-dihydro-2-furyl)-5-fluorouracil is hydrogenated.

The hydrogenation of racemic or optically active 1-(2,3-dihydro-2-furyl)-5-fluorouracil can be carried out in a manner known per se, either in the presence of a noble metal catalyst, preferably palladium on a suitable carrier such as carbon, or with Raney-nickel, in an inert organic solvent such as an ether, ester or alkanol. Ethanol is the preferred solvent, in which case the hydrogenation can be carried out either at room temperature or at an elevated temperature, conveniently the reflux temperature of the hydrogenation mixture, and under normal pressure or under an elevated hydrogen pressure. That the hydrogenation can be carried out selectively without affecting the fluorouracil portion of the molecule is surprising having regard to the relatively great lability of the fluorine atom.

The hydrogenation product obtained, namely racemic or optically active 1-(2-tetrahydrofuryl)-5-fluorouracil depending on the starting material used, can be isolated from the hydrogenation mixture in a simple manner and purified by means of customary purification techniques, most simply by recrystallisation.

The racemic or optically active 1-(2,3-dihydro-2-furyl)-5-fluorouracil used as the starting material in the foregoing process can be prepared by subjecting a compound of the general formula

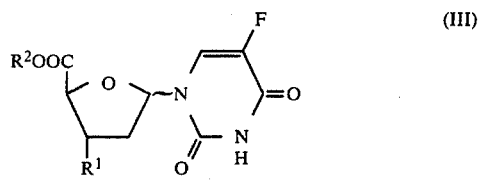

, wherein $R^1$ represents a hydroxy group or a leaving group and
$R^2$ represents a hydrogen atom or a lower alkyl, aryl-(lower alkyl) or aryl group, which can be present as the racemate or in the form of an optical antipode, to a decarboxylating β-elimination.

Compounds of the general formula

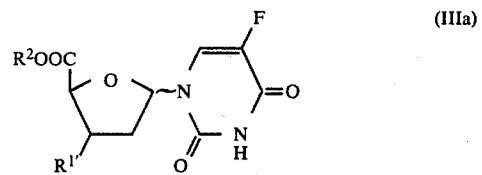

, wherein $R^{1'}$ represents a leaving group and
$R^2$ represents a hydrogen atom or a lower alkyl, aryl-(lower alkyl) or aryl group, are novel and it will be appreciated that they also form part of the present invention.

The term "leaving group" used herein denotes such groups which result from the modification of a hydroxy group (e.g. by converting same into an acyloxy group, preferably into an alkylsulphonyloxy or arylsulphonyloxy group or a phosphoric acid ester) and which can be eliminated readily.

The term "lower alkyl" used herein includes alkyl groups containing up to 6 carbon atoms. The methyl and ethyl groups are the preferred lower alkyl groups. Examples of aryl groups are the phenyl group and phenyl groups substituted by halogen or nitro. A preferred aryl-(lower alkyl) group is the benzyl group.

Sub-groups of compounds of formula III are compounds of formulae III-1, III-2 and III-3 in which $R^{1'}$ represents a leaving group and $R^{2'}$ represents a lower alkyl, aryl-(lower alkyl) or aryl group.

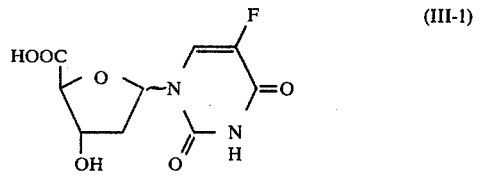

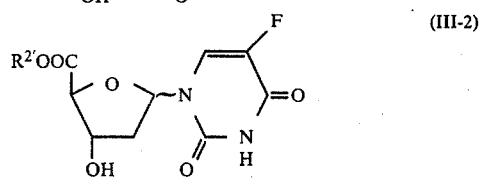

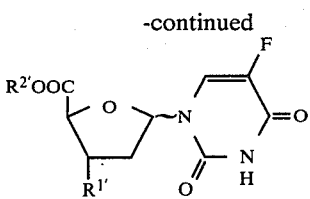

The structural formulae given herein are intended to include the compounds not only in the form of their racemate, but also in optically active form. The wavy bond in the formulae is intended to indicate that the compounds can be present as the racemate, as the anomeric mixture or in optically active form. Starting from (R)- or D- or β-5-fluoro-2'-desoxyuridine there is obtained (R)- or D- or β-1-(2-tetrahydrofuryl)-5-fluorouracil. The corresponding (S)- or L- or α-5-fluoro-2'-desoxyuridine leads to (S)- or L- or α-1-(2-tetrahydrofuryl)-5-fluorouracil.

In a preferred embodiment for the preparation of 1-(2,3-dihydro-2-furyl)-5-fluorouracil of formula II, 1-(5-carboxy-4-hydroxy-2-tetrahydrofuryl)-5-fluorouracil of formula III-1 is subjected to a decarboxylating dehydration. This can be carried out by warming the 1-(5-carboxy-4-hydroxy-2-tetrahydrofuryl)-5-fluorouracil in dimethylformamide in the presence of a dimethylformamide di(lower alkyl) acetal, preferably dimethylformamide dineopentyl acetal, to a temperature of about 50°–120° C.

1-(2,3-Dihydro-2-furyl)-5-fluorouracil of formula II can, however, also be prepared from a compound of formula III-2 or III-3. The 4'-hydroxy group in a compound of formula III-2, which compound can be obtained in a known manner by esterifying 1-(5-carboxy-4-hydroxy-2-tetrahydrofuryl)-5-fluorouracil of formula III-1 with, for example, a lower alkyl, aryl-(lower alkyl) or aryl halide, is conveniently first converted into an effective leaving group. This can be carried out by reaction with an appropriate acid derivative, preferably a sulphonic or phosphoric acid derivative and especially an alkylsulphonyl chloride or arylsulphonyl chloride such as methanesulphonyl chloride, benzenesulphonyl chloride or p-toluenesulphonyl chloride in a manner known per se; that is to say, in an anhydrous medium, in the presence of an acid binding agent, preferably pyridine or quinoline, at a temperature between ca −15° C. and +30° C., preferably at room temperature. By warming the resulting compound of formula III-3 in a slightly basic medium, preferably in aqueous pyridine, in the presence of sodium hydrogen carbonate, there is obtained 1-(2,3-dihydro-2-furyl)-5-fluorouracil of formula II, there being probably firstly formed as an intermediate the carboxylate anion of the formula

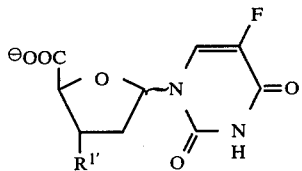

wherein $R^{1'}$ has the significance given earlier.

The (2'R)- and (2'S)-1-(2-tetrahydrofuryl)-5-fluorouracil aforesaid possess cytostatic activity. It has been found that the (2'S)-antipode is somewhat more active and less toxic, which is surprising since in the sugar series those compounds having the L-α-configuration are practically inactive even when their D-β-antipodes show good activity. 1-(2,3-Dihydro-2-furyl)-5-fluorouracil, which likewise forms part of the present invention also possesses cytostatic activity not only in racemic but also in optically active form.

The aforementioned (2'R)- and (2'S)-1-(2-tetrahydrofuryl)-5-fluorouracil as well as racemic or optically active 1-(2,3-dihydro-2-furyl)-5-fluorouracil can be used for the treatment of carcinomas of the stomach, colon, rectum and oesophagus. In the case of oral administration to adults dosages of 800–1200 mg, divided over the day may be employed. In the case of long term infusion dosages of 20 mg/kg/day are used.

(2'R)- and (2'S)-1-(2-tetrahydrofuryl)-5-fluorouracil as well as racemic or optically active 1-(2,3-dihydro-2-furyl)-5-fluorouracil can accordingly be used as medicaments in the form of pharmaceutical preparations, having direct or delayed release of the active ingredient, which contain them in association with a compatible pharmaceutical carrier material. This carrier material can be an organic or inorganic inert carrier material suitable for enteral, percutaneous or parenteral administration such as, for example, water, gelatin, gum arabic, lactose, starch, magnesium stearate, talc, vegetable oils, polyalkyleneglycols, petroleum jelly etc. The pharmaceutical preparations can be made up in a solid form (e.g. as tablets, dragees, suppositories or capsules) in a semi-solid form (e.g. as salves) or in a liquid form (e.g. as solutions, suspensions or emulsions). The pharmaceutical preparations may be sterilised and/or may contain further adjuvants such as preserving, stabilising, setting or emulsifying agents, flavour-improving agents, salts for variation of the osmotic pressure or substances acting as buffers. The pharmaceutical preparations can be prepared in a conventional manner.

The following Examples illustrate the present invention:

EXAMPLE 1

8.0 g of platinum black (freshly prepared from 10 g of platinum oxide by catalytic hydrogenation in aqueous suspension) were added to a solution of 15 g of (2'R)-1-(4-hydroxy-5-hydroxymethyl-2-tetrahydrofuryl)-5-fluorouracil (β-5-fluoro-2'-desoxyuridine) and 5.5 g of sodium hydrogen carbonate in 1.5 liters of distilled water and the mixture obtained was warmed to 80° C. (oil-bath temperature) for 16 hours while stirring and introducing oxygen. A further 0.5 g of sodium hydrogen carbonate was added and the oxidation was continued until starting material could no longer be detected in the solution (testing by thin-layer chromatography on silica gel), this being the case after about 48 hours. The mixture was cooled to 20° C., the catalyst filtered off under suction and the solution concentrated to 200 ml. This solution was added to a column containing 300 ml of Amberlite IRC-120 (H+ form), the sodium salt being converted into the free acid. The column was washed with water, the eluate concentrated to 200 ml under reduced pressure and lyophilised.

The 12.7 g of snow-white (2'R)-1-(5-carboxy-4-hydroxy-2-tetrahydrofuryl)-5-fluorouracil obtained were, without further purification, heated under reflux for 5 hours together with 250 mg of p-toluenesulphonic acid in 380 ml of absolute methanol. The precipitate which formed upon cooling to 20° C. was filtered off under suction, washed with methanol and dried. After working-up the mother liquor there was obtained a total of 11.2 g of (2'R)-1-(5-carbomethoxy-4-hydroxy-2-tetrahydrofuryl)-5-fluorouracil of melting point 250°–252° C. (decomposition).

EXAMPLE 2

16.7 g of (2'S)-1-(4-hydroxy-5-hydroxymethyl-2-tetrahydrofuryl)-5-fluorouracil (α-5-fluoro-2'-desoxyuridine) were converted into 13.8 g of (2'S)-1-(5-carboxy-4-hydroxy-2-tetrahydrofuryl)-5-fluorouracil in a manner analogous to that described in Example 1. 8.0 g of this compound were esterified in a manner analogous to that described in Example 1 to give 4.9 g of (2'S)-1-(5-carbomethoxy-4-hydroxy-2-tetrahydrofuryl)-5-fluorouracil of melting point 173°–174° C.

EXAMPLE 3

7.6 ml of methanesulphonyl chloride in 100 ml of benzene were added dropwise at room temperature and while stirring to a solution of 15.2 g of (2'R)-1-(5-carbomethoxy-4-hydroxy-2-tetrahydrofuryl)-5-fluorouracil in 300 ml of pyridine. The mixture was left to stand for 48 hours, concentrated under reduced pressure at 40° C., the residue treated with 300 ml of ice-water and the mixture obtained, after stirring for 2 hours, extracted once with 500 ml of methylene chloride and then twice with 100 ml of methylene chloride each time. The combined methylene chloride extracts were washed with cold 1-N sulphuric acid and subsequently with sodium hydrogen carbonate solution, dried over sodium sulphate and evaporated to dryness. The solid residue was washed with a small amount of cold methylene chloride and yielded 10.6 g of crystalline (2'R)-1-(5-carbomethoxy-4-methylsulphonyloxy-2-tetrahydrofuryl)-5-fluorouracil of melting point 145°–147° C. A further 2.5 g could be isolated from the mother liquor.

EXAMPLE 4

In analogy to the procedure described in Example 3, from 3.2 g of (2'S)-1-(5-carbomethoxy-4-hydroxy-2-tetrahydrofuryl)-5-fluorouracil in 60 ml of pyridine there were obtained 2.1 g of (2'S)-1-(5-carbomethoxy-4-methylsulphonyloxy-2-tetrahydrofuryl)-5-fluorouracil of melting point 188°–189° C. (from methanol).

EXAMPLE 5

1.0 g of (2'S)-1-(5-carboxy-4-hydroxy-2-tetrahydrofuryl)-5-fluorouracil was heated on a steam-bath for 10 hours in 40 ml of dimethylformamide with 3.5 ml of dimethylformamide dineopentyl acetal. The solution was evaporated under reduced pressure, the residue extracted with 50 ml of ethyl acetate, the extract again evaporated and the residue digested with 20 ml of isopropanol. After recrystallisation of the residue from ethyl acetate/n-hexane, there was obtained 0.58 g of (2'S)-1-(2,3-dihydro-2-furyl)-5-fluorouracil of melting point 183°–184° C.; $[\alpha]_D^{25} = +170°$ (ethanol, c=0.5).

EXAMPLE 6

According to the procedure described in Example 5, from 1.0 g of (2'R)-1-(5-carbomethoxy-4-hydroxy-2-tetrahydrofuryl)-5-fluorouracil there was obtained 0.53 g of (2'R)-1-(2,3-dihydro-2-furyl)-5-fluorouracil of melting point 174°–175° C. (from ethyl acetate/n-hexane); $[\alpha]_D^{25} = -205.4°$ (methanol, c=0.5).

EXAMPLE 7

A mixture of 1.0 g of (2'S)-1-(5-carbomethoxy-4-methylsulphonyloxy-2-tetrahydrofuryl)-5-fluorouracil and 0.5 g of sodium hydrogen carbonate in 20 ml of pyrimidine and 10 ml of water was heated on a steam-bath for 20 hours. The solution was then evaporated to dryness under reduced pressure, the last traces of water being removed by repeated evaporation with an azeotropic mixture of ethanol and benzene. The residue was boiled up with 100 ml of ethanol, filtered and digested with isopropanol. There was obtained 0.18 g of crystalline (2'S)-1-(2,3-dihydro-2-furyl)-5-fluorouracil of melting point 183°–184° C. (from ethyl acetate/n-hexane); $[\alpha]_D^{25} = +169°$ (ethanol, c=0.5).

EXAMPLE 8

According to the procedure described in Example 7, from 1.0 g of (2'R)-1-(5-carbomethoxy-4-methylsulphonyloxy-2-tetrahydrofuryl)-5-fluorouracil there was obtained 0.16 g of (2'R)-1-(2,3-dihydro-2-furyl)-5-fluorouracil of melting point 174°–175° C. (from ethyl acetate/n-hexane); $[\alpha]_D^{25} = -205°$ (methanol, c=0.5).

EXAMPLE 9

Manufacture of (2'S)-1-(2-tetrahydrofuryl)-5-fluorouracil

Method A

A solution of 1.0 g of (2'S)-1-(2,3-dihydro-2-furyl)-5-fluorouracil in 100 ml of ethanol was hydrogenated while heating to reflux in the presence of 200 mg of Raney-nickel which had been washed neutral. The catalyst was filtered off under suction, the solution concentrated at room temperature under reduced pressure and the (2'S)-1-(2-tetrahydrofuryl)-5-fluorouracil which crystallised out was dried; melting point 179°–180° C.; $[\alpha]_D^{25} = -50.4°$ (ethanol, c=0.5); yield: 0.73 g.

Method B 1.0 g of (2'S)-1-(2,3-dihydro-2-furyl)-5-fluorouracil was hydrogenated in 100 ml of ethanol in the presence of 50 mg of 5% palladium/carbon while shaking under normal conditions (20° C., normal pressure). After uptake of the theoretically required amount of hydrogen, the catalyst was filtered off and the clear solution concentrated at room temperature under reduced pressure. The precipitated, crystalline (2'S)-1-(2-tetrahydrofuryl)-5-fluorouracil was dried; melting point 179°–180° C.; $[\alpha]_D^{25} = -50.2°$ (ethanol, c=0.5); yield: 0.92 g.

EXAMPLE 10

According to the methods described in Example 9, from 1.0 g of (2'R)-1-(2,3-dihydro-2-furyl)-5-fluorouracil there was obtained 0.63 g of crystalline (2'R)-1-(2-tetrahydrofuryl)-5-fluorouracil of melting point 168°–170° C.; $[\alpha]_D^{25} = +48.0°$ (ethanol, c=0.3).

EXAMPLE 11

According to the procedure described in Example 5, from 2.0 g of an anomeric mixture of (2'R,S)-1-(5-carboxy-4-hydroxy-2-tetrahydrofuryl)-5-fluorouracil there was obtained 1.16 g of essentially racemic (2'R,S)-1-(2,3-dihydro-2-furyl)-5-fluorouracil of melting point 188°–190° C. (from ethyl acetate/n-hexane); $[\alpha]_D^{25} = -17.7°$ (ethanol, c=0.5), showing that the decarboxylatin dehydration proceeded slightly asymmetrically.

EXAMPLE 12

According to the procedure described in Example 7, from 2.0 g of an anomeric mixture of (2'R,S)-1-(5-carbomethoxy-4-methylsulphonyloxy-2-tetrahydrofuryl)-5-fluorouracil there were obtained 0.81 g of crystalline, essentially racemic (2'R,S)-1-(2,3-dihydro-2-furyl)-5-fluorouracil of melting point 187°–189° C. (from ethyl acetate/n-hexane); $[\alpha]_D^{25} = -11.8°$ (ethanol, c=0.5), showing that the decarboxylating β-elimination proceeded slightly asymmetrically.

EXAMPLE 13

Manufacture of (2'R,S)-1-(2-tetrahydrofuryl)-5-fluorouracil 2.0 g of racemic (2'R,S)-1-(2,3-dihydro-2-furyl)-5-fluorouracil were selectively hydrogenated according to each of the methods described in Example 9 to give racemic (2'R,S)-1-(2-tetrahydrofuryl)-5-fluorocytosine of melting point 168°–169° C.; $[\alpha]_D^{25} = +3.2°$ (ethanol, c=0.5). The hydrogenation proceeded sligthly asymmetrically.

I claim:
1. A compound of the formula

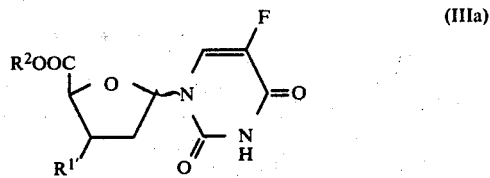

(IIIa)

wherein R$^{1'}$ is a leaving group selected from methylsulphonyloxy, phenylsulphonyloxy, p-toluenesulphonyloxy or phosphoric acid ester and R$^2$ is hydrogen, C$_{1-6}$ lower alkyl, aryl-(lower alkyl) or aryl where aryl is phenyl or phenyl substituted by halogen or nitro said compound being present as the racemate or in the form of an optical antipode.

2. The compound of claim 1 which is (2'R)-1-(5-carbomethoxy-4-methylsulphonyloxy-2-tetrahydrofuryl)-5-fluorouracil.

3. The compound of claim 1 which is (2'S)-1-(5-carbomethoxy-4-methylsulphonyloxy-2-tetrahydrofuryl)-5-fluorouracil.

* * * * *